United States Patent
Proano

(10) Patent No.: US 10,440,686 B2
(45) Date of Patent: Oct. 8, 2019

(54) DYNAMIC ALLOCATION OF MULTIPLE WIRELESS INTERFACES IN AN IMAGING DEVICE

(71) Applicant: VAREX IMAGING CORPORATION, Salt Lake City, UT (US)

(72) Inventor: Cesar Proano, Palo Alto, CA (US)

(73) Assignee: VAREX IMAGING CORPORATION, Salt Lake City, UT (US)

( * ) Notice: Subject to any disclaimer, the term of this patent is extended or adjusted under 35 U.S.C. 154(b) by 31 days.

(21) Appl. No.: 15/822,139

(22) Filed: Nov. 25, 2017

(65) Prior Publication Data

US 2019/0166585 A1 May 30, 2019

(51) Int. Cl.

| | |
|---|---|
| *H04W 72/04* | (2009.01) |
| *H04N 7/06* | (2006.01) |
| *A61B 6/00* | (2006.01) |
| *H01Q 21/28* | (2006.01) |
| *H01Q 21/30* | (2006.01) |
| *G06T 7/00* | (2017.01) |
| *H04W 84/12* | (2009.01) |
| *H04W 88/08* | (2009.01) |
| *H01Q 21/20* | (2006.01) |

(52) U.S. Cl.
CPC ........... *H04W 72/04* (2013.01); *A61B 6/4233* (2013.01); *A61B 6/56* (2013.01); *H01Q 21/28* (2013.01); *H01Q 21/30* (2013.01); *H04N 7/063* (2013.01); *H04N 7/066* (2013.01); *G06T 7/0012* (2013.01); *G06T 2207/10116* (2013.01); *H01Q 21/205* (2013.01); *H04W 84/12* (2013.01); *H04W 88/08* (2013.01)

(58) Field of Classification Search
CPC .... H04B 17/24; H04B 17/318; H04B 17/345; H04L 1/0003; H04L 1/0026; H04L 25/0204
See application file for complete search history.

(56) References Cited

U.S. PATENT DOCUMENTS

| | | | |
|---|---|---|---|
| 2009/0034683 A1 | 2/2009 | Tamakoshi | |
| 2010/0246757 A1 | 9/2010 | Liu et al. | |
| 2015/0327132 A1* | 11/2015 | Shen | H04W 48/18 370/252 |
| 2016/0166227 A1* | 6/2016 | Tanaka | A61B 6/563 |
| 2017/0025761 A1 | 1/2017 | Kim et al. | |

* cited by examiner

*Primary Examiner* — Ayaz R Sheikh
*Assistant Examiner* — Debebe A Asefa
(74) *Attorney, Agent, or Firm* — Su IP Consulting

(57) ABSTRACT

An X-ray imaging device includes a first wireless communication module coupled to a first set of antennas; a second wireless communication module coupled to a second set of antennas; and a controller that is coupled to the first wireless communication module and the second wireless communication module. The controller is configured to receive a first value for a wireless performance metric for the first wireless communication module while the X-ray imaging device, receive a second value for the wireless performance metric for the second wireless communication module while the X-ray imaging device, based on the first value and the second value, determine a first wireless communication function to be performed by the first wireless communication module, and cause the first wireless communication module to perform the first wireless communication function.

24 Claims, 5 Drawing Sheets

DYNAMIC ALLOCATION OF MULTIPLE WIRELESS INTERFACES IN AN IMAGING DEVICE

BACKGROUND

Unless otherwise indicated herein, the approaches described in this section are not prior art to the claims in this application and are not admitted to be prior art by inclusion in this section.

Digital radiography is a form of X-ray imaging in which digital X-ray sensors are used to generate digital images, and has multiple advantages over traditional film-based techniques. By bypassing chemical processing, digital radiography is more time efficient, provides digital images for immediate image preview, facilitates image enhancement, and generally requires less radiation to produce an image of similar contrast.

Digital radiography is now used in many applications, including medical diagnostics, veterinary care, dental imaging, industrial inspection, and security. Each of these applications can benefit from a fully portable flat panel X-ray sensor that is not physically tethered to the associated workstation or computer that receives acquired images, performs image processing and enhancement, and provides a user interface for controlling image acquisition. Consequently, flat panel X-ray sensors have been developed with a form factor that can be manually positioned for X-ray image acquisition and easily carried between locations for use at different workstations. In addition, some flat panel X-ray sensors are configured for wireless communication with the currently associated workstation for transferring image data to the workstation and receiving control inputs from the workstation. Thus, during normal use, such flat panel X-ray sensors are not physically coupled to an external workstation or computer.

SUMMARY

In accordance with at least some embodiments of the present disclosure, an X-ray imaging device comprises a first wireless communication module coupled to at least one antenna in a first set of antennas that is disposed within a first region of the device; a second wireless communication module coupled to at least one antenna in a second set of antennas that is disposed within a second region of the X-ray imaging device; and a controller that is coupled to the first wireless communication module and the second wireless communication module. The controller is configured to receive a first value for a wireless performance metric for the first wireless communication module while the X-ray imaging device is disposed in a current location; receive a second value for the wireless performance metric for the second wireless communication module while the X-ray imaging device is disposed in the current location; based on the first value and the second value, determine a first wireless communication function to be performed by the first wireless communication module; and cause the first wireless communication module to perform the first wireless communication function.

In accordance with at least some embodiments of the present disclosure, a method of allocating multiple wireless interfaces for an X-ray imaging device that includes a first wireless communication module and a second wireless communication module comprises receiving a first set of wireless performance metrics for the first wireless communication module the X-ray imaging device is disposed in a current location; receiving a second set of wireless performance metrics for the second wireless communication module while the X-ray imaging device is disposed in the current location; based on the first set of wireless performance metrics and the second set of wireless performance metrics, determining a first wireless communication function to be performed by the first wireless communication module; and causing the first wireless communication module to perform the first wireless communication function.

In accordance with at least some embodiments of the present disclosure, a system comprises a first wireless communication means; a second wireless communication means; means for receiving a first set of wireless performance metrics for the first wireless communication module of the X-ray imaging device; means for receiving a second set of wireless performance metrics for the second wireless communication module of the X-ray imaging device; based on the first set of wireless performance metrics and the second set of wireless performance metrics, means for determining a first wireless communication function to be performed by the first wireless communication module; and means for causing the first wireless communication module to perform the first wireless communication function.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The foregoing and other features of the present disclosure will become more fully apparent from the following description and appended claims, taken in conjunction with the accompanying drawings. These drawings depict a few embodiments in accordance with the disclosure and are, therefore, not to be considered limiting of its scope. The disclosure will be described with additional specificity and detail through use of the accompanying drawings.

DETAILED DESCRIPTION

Figure 1:
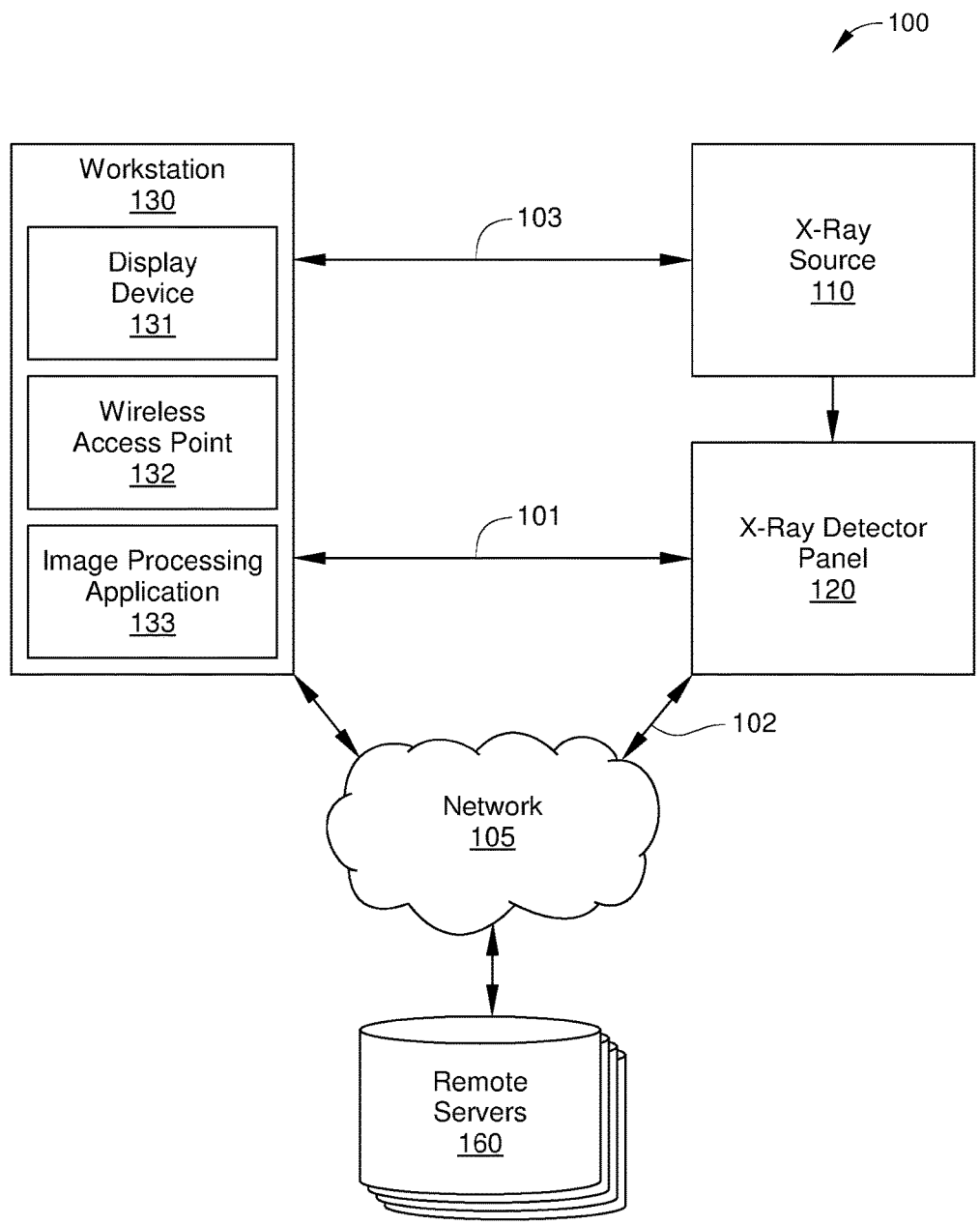
FIG. 1 is a block diagram of a digital radiographic system, according to one or more embodiments of the present disclosure.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the disclosure, as generally described herein, and illustrated in the figures, can be arranged, substituted, combined, and designed in a wide variety of different configurations, all of which are explicitly contemplated and make part of this disclosure.

In many applications of digital radiography, such as in a hospital environment, a single flat panel X-ray sensor is shared between multiple image acquisition workstations. Wireless communications are now the preferred method for controlling and downloading image data from such X-ray sensors. This is because using a cable connection suffers from significant drawbacks, including the creation of trip hazards when in use, the potential for the cable being lost or damaged, and mechanical and/or electrical deterioration of the cable that occurs each time the cable is inserted or removed. But while wirelessly controlling an X-ray sensor and downloading image data from the X-ray sensor is convenient, a fast and reliable connection is generally necessary. Specifically, only a reliable wireless connection should be employed when controlling an X-ray imaging device, since medical devices must be very robust in operation. In addition, a reliable wireless connection reduces the likelihood of losing acquired image data when such data are uploaded from the X-ray imaging device, thereby avoiding the additional dosing caused by acquiring duplicate images or re-transmitted and previous saved images. Further, a high-bandwidth connection enables efficient transfer of images generated by the X-ray imaging device, which increases utilization of the device and reduces the likelihood of image data loss.

However, the hospital environment presents numerous challenges for using wireless communications in a fast and reliable manner to control an X-ray imaging device and to download data from the X-ray imaging device. First, many devices in hospitals currently employ some form of wireless interface. Therefore, a wireless connection to an X-ray imaging device rarely has a dedicated frequency channel, and instead typically shares a channel with other wireless devices located nearby. As a result, some channels can provide more bandwidth than others, depending on how channels are being shared among wireless devices.

Second, the conventional radiography film cassettes that are being replaced by wireless digital radiographic equipment are employed with a wide range of metallic accessories, which can interrupt and/or reflect radio frequency (RF) signals. For example, a bucky is a metallic drawer-like device disposed beneath an X-ray imaging table for holding the X-ray film cassette in a conventional radiography system. It as become common practice for buckies to be employed in holding digital X-ray imaging devices in place beneath the X-ray imaging table in lieu of a conventional film cassette. Because a typical bucky can act as a Faraday cage, RF signals to and from a wireless X-ray imaging device held inside a bucky can be greatly attenuated or even blocked completely. Thus, while a room in a hospital can have a strong wireless signal present, the actual location of the X-ray imaging device during use may not.

Third, every hospital or clinic has distinct characteristics that generate a unique and often highly variable RF environment for wireless devices located therein. For example, the number of wireless access points (APs) and the distance between the APs varies from hospital to hospital. In addition, the number and type of objects disposed between the nearest AP and a particular wireless device is highly variable, and therefore wireless signal strength available for a particular wireless device cannot be predicted based only on distance to the nearest AP. Further, the number of devices sharing a particular channel can vary greatly over time. As a result, signal strength and reliability can vary unpredictably from hospital to hospital, and even in the same location in the same hospital at different times. Consequently, as an X-ray imaging device is moved from one room to another, the strength and reliability of the wireless connection to the X-ray imaging device can fluctuate significantly.

In light of the above, there is a need in the art for devices, systems, and methods to optimize or otherwise improve a wireless connection to an imaging device in a medical imaging environment, such as an X-ray sensor.

According to various embodiments of the present disclosure, a portable X-ray detector panel includes multiple wireless communication modules to enhance the wireless performance of the X-ray detector panel. Each wireless communication module is coupled to one or more respective antennas that are each disposed in a different portion or region of the X-ray detector panel. Consequently, each wireless communication module will have different reception/transmission capabilities, depending on orientation to and distance from the nearest wireless access point (AP), objects blocking or reflecting radio frequency (RF) signal from the one or more antennas, multipath of the RF signal (reflection) and the current channel/band occupancy in the vicinity. A controller in the X-ray detector panel is configured to cause the multiple wireless communication modules to periodically or continuously survey the surrounding wireless environment by checking one or more wireless performance metrics, such as signal strength, data transfer rate, package retransmission rate, and the like. The controller is further configured to dynamically allocate each of the wireless communication modules to a different wireless function based on the wireless performance metrics measured for each. As a result, when the strength or reliability of wireless connections available to the X-ray detector panel changes (such as when the X-ray detector panel is moved to a new location), the controller can reallocate the wireless communication modules to perform different wireless functions. For example, the controller can employ the wireless communication module with higher performance metric values to perform high bandwidth tasks, such as uploading image data, and the wireless communication module with lower performance metric values to perform low bandwidth tasks, such as transmitting and receiving control signals.

FIG. 1 is a block diagram of a digital radiographic system 100, according to one or more embodiments of the present disclosure. Digital radiographic system 100 is configured to generate a digital X-ray image, and includes an X-ray source 110, an X-ray detector panel 120 (sometimes referred to as a digital image receptor), a workstation 130, and a network 105. Digital radiographic system 100 generates a digital X-ray image when X-ray photons, generated by X-ray source 110, pass through a patient, sample, or other object, and are incident on X-ray detector panel 120. As X-ray photons pass through the object of interest, internal structures of the object cause spatial variations in the intensity of X-ray photons actually incident on X-ray detector panel 120. In indirect detection, X-ray detector panel 120 converts the incident X-ray photons to visible or other light photons via a scintillator, and a photodiode layer generates charge which is then converted to a digital output signal thru an analog-to-digital converter (ADC) based on the light photons. The digital output signal can then be transmitted wirelessly to workstation 130 via a wireless connection 102 for subsequent image processing, analysis, and storage. Alternatively or additionally, the digital output signal can be transmitted via a wireless connection 102 and network 105 to one or more remote servers 160.

Workstation 130 may be any technically feasible computing device that includes a display device for displaying a user interface (UI) and is capable of wirelessly connecting to X-ray detector panel 120. For example, in some embodiments, workstation 130 may be desktop or laptop computer that is configured to interact with (e.g., receive output from and provide input to) X-ray detector panel 120. In other embodiments, workstation 130 may be a mobile computing device, such as a smartphone, a wearable computing device, or an electronic tablet. In either case, workstation 130 includes a wireless access point 132. In some embodiments, in some embodiments, workstation 130 is programmed with an image processing application 133 for processing image data received from X-ray detector panel 120. Image processing application 133 may be configured to convert a digital representation or other image data into a digital image in a specific image file format and/or to modify the resultant digital image. Thus, once a digital representation is received from X-ray detector panel 120, image generation and post-processing can be performed independently from the operation of X-ray detector panel 120. For example, image processing application 133 may provide image processing capability for radiographic (still-picture X-ray) applications and/or fluoroscopic (video X-ray) applications.

Workstation 130 may be further configured to query, over a network, a list of patients and studies to be performed, such as a Digital Image and Communications in Medicine (DICOM) Modality Worklist Server or other remote server 160; to locally store a list of patients and studies to be performed, similar to a DICOM Modality Worklist Server; to provide a user interface to access a locally stored patient/study list; to maintain a local record of studies performed and images acquired, such as a panel-resident version of a DICOM picture archiving and communication system (PACS); to provide a user interface to view and/or review such studies; and to transmit studies performed, including images, directly to one or more remote servers 160. In operation, workstation 130 is configured to transmit control signals to and receive control signals from X-ray detector panel 120 and X-ray source 110, and to execute image processing application 133. Workstation 130 communicates wirelessly with X-ray detector 120 via a wireless connection 101 (also referred to as a wireless interface) and with X-ray source 110 via a wireless connection 103 (also referred to as a wireless interface).

X-ray source 110 can be any suitable X-ray source for emitting X-ray photons, such as an X-ray tube (or tube generator). Generally, X-ray source 110 is controlled by workstation 130 or another computing device, via a wired or wireless connection 103. Specifically, workstation 130 enables selection of X-ray attributes suitable for a specific image acquisition or acquisition session. For example, workstation 130 can control the power supply of X-ray source 110, thereby producing a desired peak kilovoltage (kVp), current, and duration of exposure.

X-ray detector panel 120 is an X-ray imaging device that is typically battery powered and operable to be communicatively connected to workstation 130. As described herein, X-ray detector panel 120 is configured to dynamically allocate multiple wireless interfaces, based on wireless performance metrics that are measured in real-time for each of multiple wireless communication modules. In this way, robust wireless communication between X-ray detector panel 120 and workstation 130 and/or network 105 is enabled. Network 105 may be any technically feasible type of communications network that allows data to be exchanged between X-ray detector panel 120 and external entities or devices, such as workstation 130, and/or one or more remote servers 160. Examples of network 105 may include a wide area network (WAN), a local area network (LAN), a wireless (WiFi) network, and/or the Internet, among others. In normal operation, X-ray detector panel 120 is communicatively coupled to network 105 via wireless connection 102 and/or to workstation 130 via wireless connection 101. One embodiment of X-ray detector panel 120 is described below in conjunction with FIG. 2.

Figure 2:
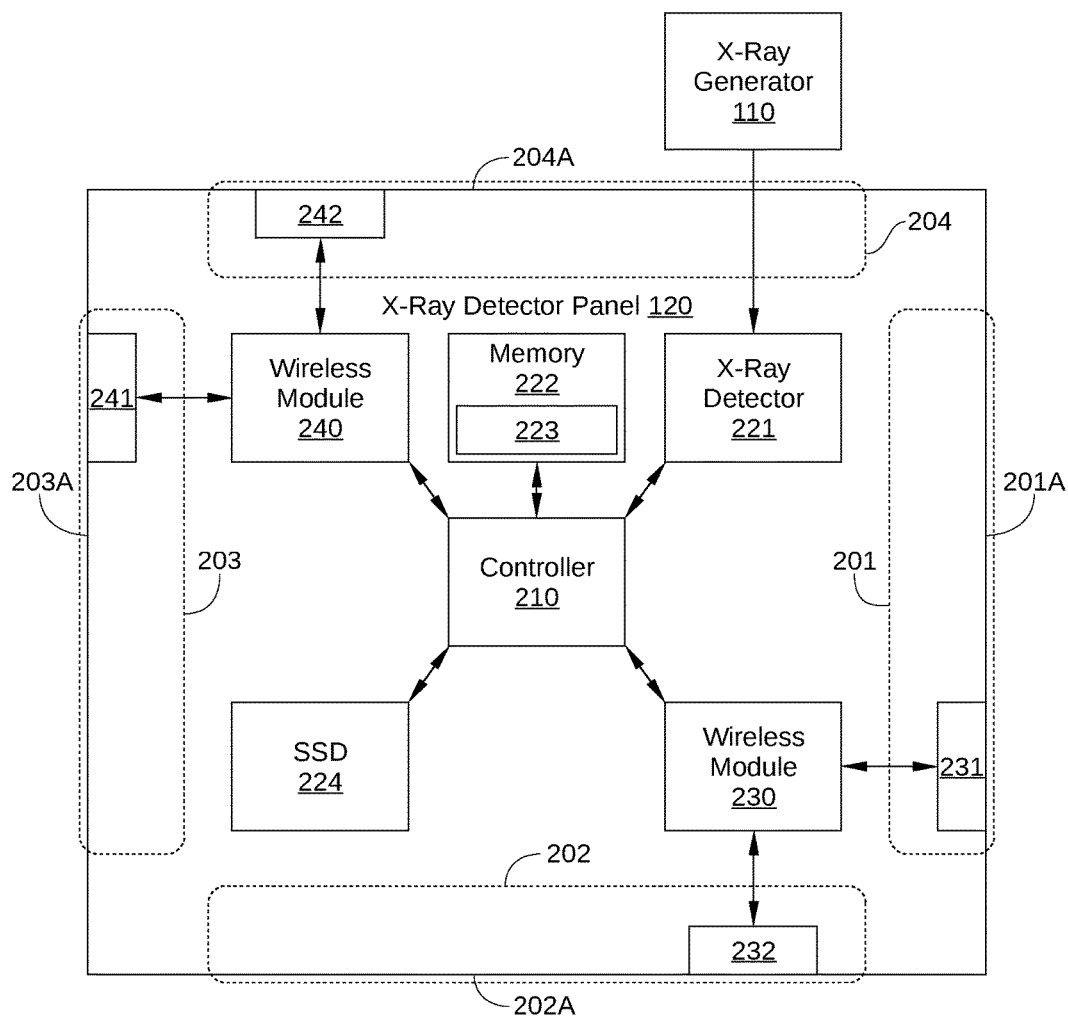
FIG. 2 is a block diagram of the X-ray detector panel of the digital radiographic system in FIG. 1, according to one or more embodiments of the present disclosure.

FIG. 2 is a block diagram of X-ray detector panel 120, according to one or more embodiments of the present disclosure. X-ray detector panel 120 can include a controller 210, an X-ray sensor 221, a memory 222, a solid-state drive (SSD) 224 or other non-volatile data storage medium, and wireless modules 230 and 240. In some embodiments, X-ray detector panel 120 includes three or more wireless modules rather than the two wireless modules shown in FIG. 2.

Controller 210 may be any suitable processor implemented as a central processing unit (CPU), an application-specific integrated circuit (ASIC), a field programmable gate array (FPGA), any other type of processing unit, or a combination of different processing units. In general, controller 210 may be any technically feasible hardware unit capable of processing data, controlling the image acquisition hardware of X-ray detector panel 120, and dynamically allocating wireless modules 230 and 240 for wireless functions as described herein. Thus, controller 210 is configured to receive a first set of wireless performance metrics from wireless module 230, a second set of wireless performance metrics from first wireless module 240, and, based on the first and second sets of wireless performance metrics, determine a first wireless function to be performed by the first wireless communication module and a second wireless function to be performed by the second wireless communication module. In addition, controller 210 is configured to control or otherwise cause wireless module 230 to perform the first wireless communication function and wireless module 240 to perform the second wireless communication function. In some embodiments, controller 210 is a CPU that executes a wireless interface allocation application 223 residing in memory 222, and in other embodiments, controller 210 includes wireless interface allocation logic implemented as hardware and/or firmware (not shown).

X-ray sensor 221 includes a matrix or array of pixel detector elements that each convert incident X-ray photons to electrical charge. In embodiments in which X-ray detector panel 120 is configured as an indirect flat panel detector, a scintillator material in X-ray detector panel 120 is excited by incident X-rays and emits light, which is detected by a plurality of photodiodes. Each diode generates a signal (e.g., a voltage that is proportional to incident light intensity) for a different pixel of what will eventually become a digital image, and each of these voltages is interpreted as a value that is proportional to the voltage. One such embodiment of X-ray sensor 221 is illustrated in FIG. 3.

Figure 3:
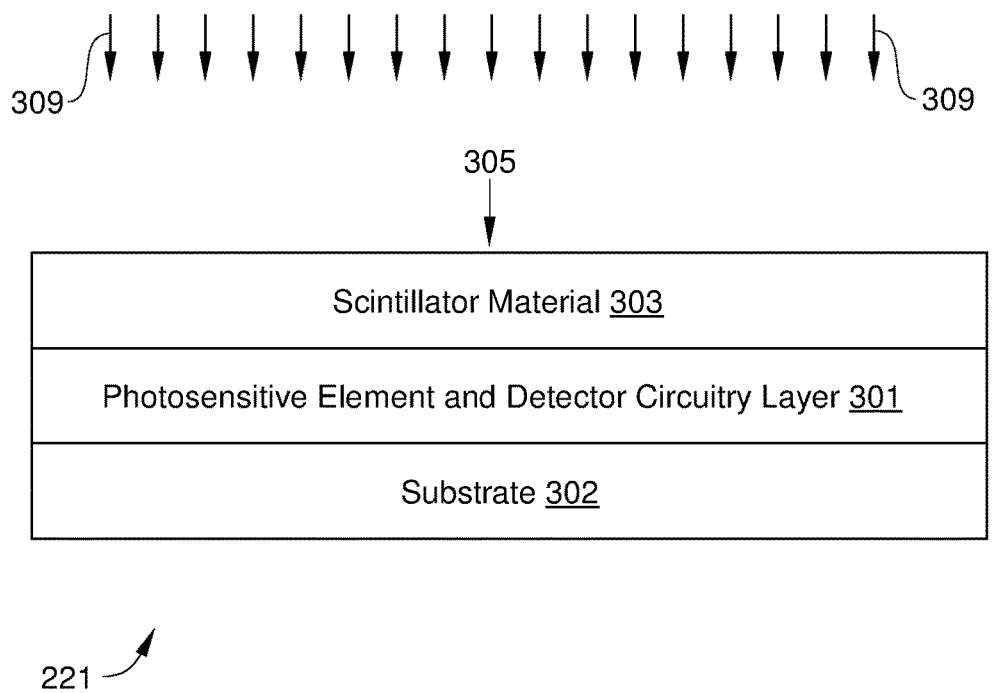
FIG. 3 schematically illustrates a cross-sectional view of an X-ray sensor panel of the flat-panel detector of FIG. 2, according to one embodiment of the disclosure.

FIG. 3 schematically illustrates a cross-sectional view of X-ray sensor 221, according to one embodiment of the disclosure. As shown, X-ray sensor 221 includes a photosensitive element and detector circuitry layer 301 formed on a substrate 302 and a layer of scintillator material 303 formed on photosensitive element and detector circuitry layer 301. Also shown are incident X-rays 309 that have passed through a patient, sample, or other object of interest after being generated by X-ray source 110. Together, photosensitive element and detector circuitry layer 301, substrate 302, and scintillator material 303 form an X-ray imaging matrix 305. It is noted that photosensitive element and detector circuitry layer 301 is generally formed from a plurality of processing layers, and that X-ray imaging matrix 305 may include additional material layers not illustrated in FIG. 3.

Photosensitive element and detector circuitry layer 301 generally includes a plurality of photosensitive elements, such as photodiodes, photogates, phototransistors, or any other suitable circuitry suitable for operation as pixel detector elements in X-ray sensor 221. For example, photosensitive element and detector circuitry layer 301 may also include thin-film transistors (TFTs) for reading out the digital signals from the pixel detector elements. Scintillator material 303 may include one or more material layers including, but no limited to, gadolinium oxisulfide ($Gd_2O_2S$:Tb), cadmium tungstate ($CdWO_4$), bismuth germanate ($Bi_4Ge_3O_{12}$ or BGO), cesium iodide (CsI), or cesium iodide thallium (CsI:Tl)), among others.

In the embodiment illustrated in FIG. 3, X-ray sensor 221 is depicted as an indirect flat panel detector, in which X-ray photons are converted to other light photons that are in turn detected and converted into charge. In other embodiments, X-ray sensor 221 can be a direct flat panel detector. In a direct flat panel detector, incident X-ray photons are converted directly into charge in an amorphous selenium layer, and the resultant charge pattern therein is read out by suitable hardware, such as a thin-film transistor (TFT) array, an active matrix array, microplasma line addressing, or the like.

Referring to FIG. 2, memory 222 may include a random access memory (RAM) module, a flash memory unit, or any other type of memory unit or combination thereof. Memory 222 includes various software programs that can be executed by controller 210 and application data associated with said software programs, including wireless interface allocation application 223, one or more image processing applications (not shown), and/or workstation configuration applications (not shown). SSD 224 provides non-volatile storage for previously acquired data or medical images, studies associated with a particular patient or project, and/or software applications. The X-ray detector panel 120 may include other components for location detection and/or motion detection (not shown), such as a position sensor, an accelerometer, a bar code reader, a color scanner, a radio-frequency identification (RFID) reader, and/or some other near-field communication device Wireless module 230 may be any technically feasible wireless chip, card, or other device that enables X-ray detector panel 120 to communicate wirelessly with workstation 130 in FIG. 1, with other workstations 130 not shown in FIG. 1, and/or with one or more APs (not shown) associated with network 105. Thus, wireless module 230 is configured to generate any suitable and technically feasible wireless interface with an external computing device, including, without limitation, a WiFi interface, a Bluetooth interface, a ZigBee interface, a WiMax interface, and the like. Examples of devices suitable for use as wireless module 230 or 240 include a Wifi module, a wireless local area network (WLAN) module, a 3rd Generation Partnership Project (3GPP) module, and the like. For example, in some embodiments, wireless module 124 is an Institute of Electrical and Electronics Engineers (IEEE) 802.11ac/n device capable of providing a WiFi Direct connection to an external device, such as a wireless AP in workstation 130 or network 105. Alternatively or additionally, in some embodiments, wireless module 124 is a device capable of providing multiple wireless interfaces to one or more external devices, such as a suitably configured electronic tablet, smartphone, or other user access device. Thus, in some embodiments, wireless module 230 is capable of simultaneous WiFi and Bluetooth operation, or WiFi and Zig Bee operation, or Bluetooth and WiMax operation, etc. Alternatively or additionally, wireless module 230 is a device capable of any technically feasible dual-band WiFi capability, in which RF signals are transmitted and received via two different frequencies (e.g., 2.5 GHz and 5.0 GHz). Alternatively or additionally, wireless module 230 is configured for operation using multiple-input and multiple-output (MIMO) to multiply the capacity of wireless connection 101, 102, and/or 103. Wireless module 230 is programmed with or otherwise includes the suitable communication protocols that enable the above-described wireless functionality.

In some embodiments, wireless module 240 is substantially identical in configuration and operation to wireless module 230. In other embodiments, wireless module 240 can have more wireless capability or less wireless capability than wireless module 230.

In the embodiment illustrated in FIG. 2, wireless module 230 is coupled to two different antennas 231 and 232, which are each disposed in a different region or portion of X-ray detector panel 120. Thus, antenna 231 is disposed in a first region 201 and antenna 232 is disposed in a second region 202. In general, antennas 231 and 232 are positioned so that wireless module 230 has different reception/transmission capabilities via each of antennas 231 and 232. To that end, antenna 231 has a different location and a different orientation than second antenna 232. For example, in the embodiment illustrated in FIG. 2, first region 201 includes a first side 201A of X-ray detector panel 120 and second region 202 includes a second side 202A of X-ray detector panel 120. Similarly, wireless module 240 is coupled to two different antennas 241 and 242, which are each disposed in a different region or portion of X-ray detector panel 120: antenna 241 is disposed in a third region 203 that includes a third side 203A of X-ray detector panel 120 and antenna 242 is disposed in a fourth region 204 that includes a fourth side 204A of X-ray detector panel 120.

In the embodiment illustrated in FIG. 2, antennas 231, 232, 241 and 242 are disposed on different sides 201A, 202A, 203A, and 204A of X-ray detector panel 120, respectively. It is noted that sides 201A, 202A, 203A, and 204A can be any surface of X-ray detector panel 120 or any region proximate a surface of X-ray detector panel 120, including edge surfaces or regions or corner surfaces or regions. It is further noted that wireless modules 230 and 240 can each be coupled to any technically feasible number of antennas, and not just two antennas apiece, as shown in FIG. 2.

In the embodiment illustrated in FIG. 2, antennas 231 and 232 are disposed on different sides of X-ray detector panel 120 than antennas 241 and 242. As a result, wireless module 230 can have significantly different wireless performance than wireless module 240, particularly in a hospital environment, in which the orientation of a particular antenna with respect to nearby wireless APs can strongly affect the wireless performance of the wireless module coupled to that particular antenna. In other embodiments, antennas coupled to a first wireless module of X-ray detector panel 120 are substantially co-located with antennas coupled to a second wireless module of X-ray detector panel 120. One such embodiment is illustrated in FIG. 4.

Figure 4:
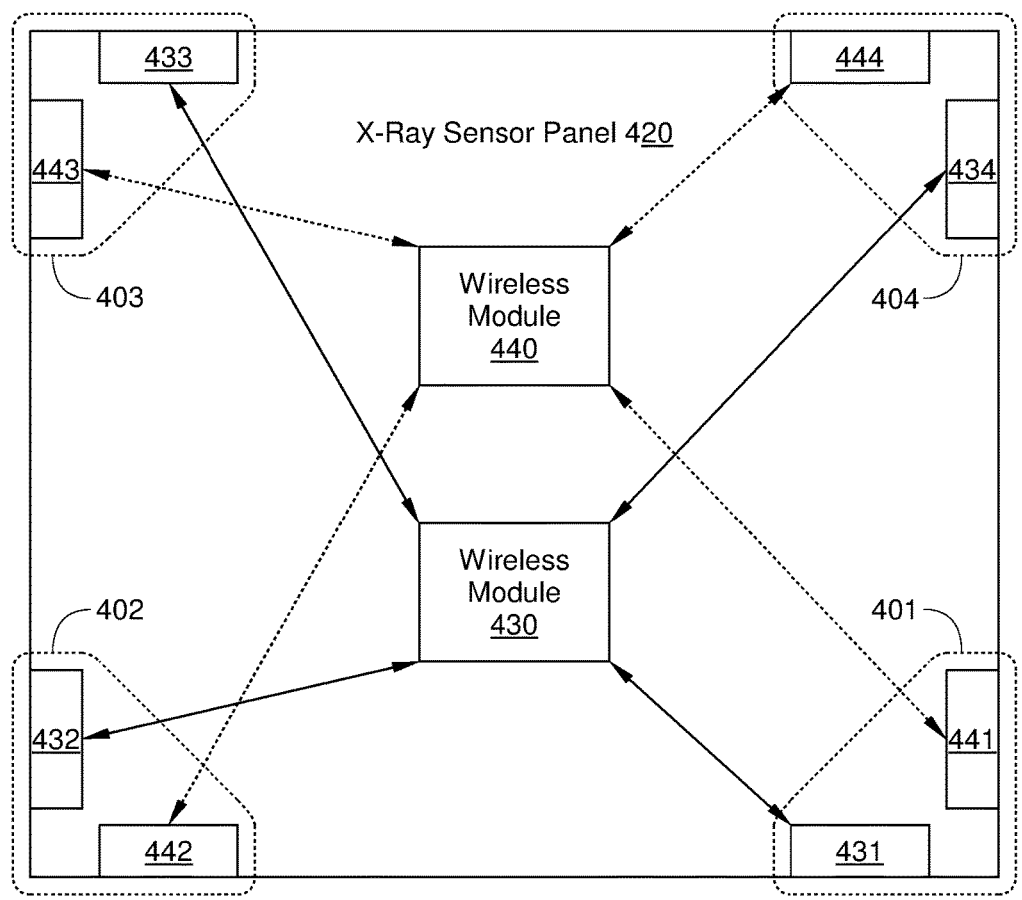
FIG. 4 is a block diagram of an X-ray detector panel that includes co-located antenna, according to one or more embodiments of the present disclosure.

FIG. 4 is a block diagram of an X-ray detector panel 420 that includes co-located antenna, according to one or more embodiments of the present disclosure. X-ray detector panel 420 is similar in configuration and operation to X-ray detector panel 120, and for clarity common features are excluded from FIG. 4. X-ray detector panel 420 includes a first wireless module 430 and a second wireless module 440. As shown, first wireless module 430 is coupled to antennas 431, 432, 433, and 434 that are each respectively disposed in regions 401-404 of X-ray detector panel 420. Similarly, second wireless module 440 is coupled to antennas 441, 442, 443, and 444 that are each respectively disposed in regions 401-404 of X-ray detector panel 420. It is noted that each of regions 401-404 only includes a single antenna coupled to first wireless module 430 and a single antenna coupled to second wireless module 440. As a result, the respective orientations of antennas 431, 432, 433, and 434 is similar to those of antennas 441, 442, 443, and 444, and the wireless performance of wireless module 430 may be similar to the wireless performance of wireless module 440.

In some embodiments, controller 210 of X-ray detector panel 420 may be configured to determine which antenna coupled to wireless module 430 has the best wireless performance metric values and which antenna coupled to wireless module 440 has the best wireless performance metric values. In such embodiments, controller 210 can then divide the transmission of data, such as image data, between the antennas coupled to wireless module 430 determined to have the best wireless performance metric value and the antenna coupled to wireless module 440 determined to have the best wireless performance metric value. In this way, transmission time for uploading large quantities of data from X-ray detector panel 420 can be reduced by a factor of two.

Alternatively or additionally, in some embodiments, wireless module 430 is configured with different wireless capabilities than wireless module 440. For example, in some embodiments, wireless module 430 is configured with Bluetooth capability and wireless module 440 is configured with dual band or single band WiFi capability. In such embodiments, controller 210 of X-ray detector panel 420 may be configured to determine which of wireless module 430 or wireless module 440 has the best wireless performance based on one or more wireless performance metrics (described below). Controller 210 then controls the wireless module with the best wireless performance to perform certain wireless communication functions that benefit from the higher wireless performance. In addition, controller 210 controls the wireless module with the lower wireless performance to perform wireless communication functions that are less impacted by lower wireless performance and/or signal strength. For example, in some embodiments, controller 210 employs the wireless module with the higher wireless performance for transmitting image data to workstation 130 and/or to network 105, and employs the wireless module with lower wireless performance for transmitting control signals to and receiving control signals from workstation 130 and/or a suitably configured user access device.

Figure 5:
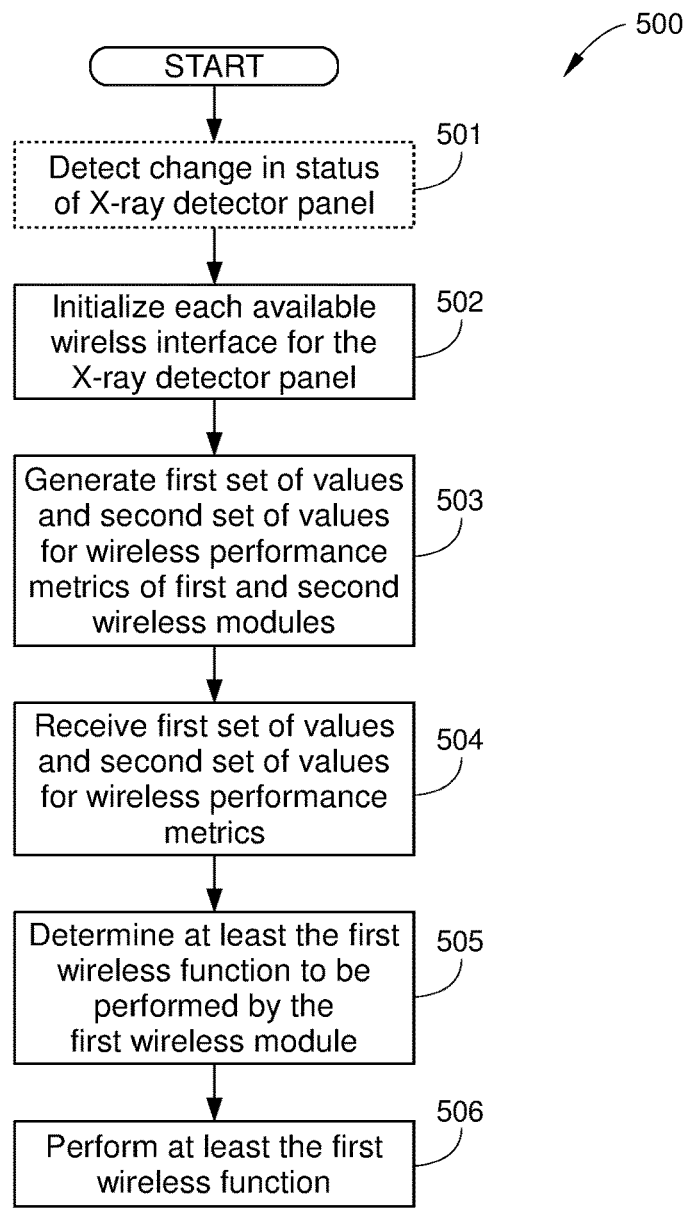
FIG. 5 sets forth a flowchart of an example method for allocating multiple wireless interfaces for an X-ray imaging device, according to one or more embodiments of the present disclosure.

FIG. 5 sets forth a flowchart of an example method for allocating multiple wireless interfaces for an X-ray imaging device, according to one or more embodiments of the present disclosure. The method may include one or more operations, functions, or actions as illustrated by one or more of blocks 501-505. Although the blocks are illustrated in a sequential order, these blocks may be performed in parallel, and/or in a different order than those described herein. Also, the various blocks may be combined into fewer blocks, divided into additional blocks, and/or eliminated based upon the desired implementation. Although the method is described in conjunction with the systems of FIGS. 1-4, persons skilled in the art will understand that any suitably configured radiographic system is within the scope of the invention.

A method 500 begins at optional step 501, in which controller 210 detects a change in status of X-ray detector panel 120. One change in status of X-ray detector panel 120 that can be detected by controller 210 includes a change from a lower power state (e.g., off, sleep, hibernate, and the like) to a normal operating state, in which X-ray detector panel 120 is operable to acquire digital X-ray images. Another example of a change in status of X-ray detector panel 120 that can be detected by controller 210 (e.g., using an accelerometer) includes a change in location of X-ray detector panel 120. In some embodiments, controller 210 detects a change in location of X-ray detector panel 120 by receiving an input indicating the location change. The input can be a user input received from a button or switch included in X-ray detector panel 120, or from a graphical user interface displayed on, for example, display device 141. Alternatively or additionally, the input can be an input received when X-ray detector panel 120 is associated with a different workstation 130 or a different location. For example, when X-ray detector 120 is relocated, a bar code reader, a color scanner, a radio-frequency identification (RFID) reader, or some other near-field communication device included in X-ray detector panel 120 can detect the new location and generate the input. Another example of a change in status of X-ray detector panel 120 that can be detected by controller 210 includes the association of X-ray detector panel 120 with a different workstation 130.

In step 502, controller 210 initializes each of the available wireless interfaces for X-ray detector panel 120. That is, each wireless module of X-ray detector panel 120 searches for available network connections for each possible interface. In embodiments in which X-ray detector panel 120 includes two wireless communication modules (for example wireless modules 230 and 240) that are each coupled to a single antenna and are configured for single-band operation, the total number of available wireless interfaces is two. In embodiments in which the first wireless module is coupled to two antennas and the second wireless module is coupled to two different antennas, the total number of available wireless interfaces is four. In embodiments in which the first wireless module is coupled to two antennas, the second wireless module is coupled to two different antennas, and each wireless module is configured for dual-band operation (e.g., 2.5 GHz and 5.0 GHz), the total number of available wireless interfaces is eight, since two wireless interfaces can be supported by each antenna.

In some embodiments, step 502 is performed in response to the detection of a change in status of X-ray detector panel 120 in step 501. Additionally or alternatively, in some embodiments, step 502 is performed periodically by X-ray detector panel 120. Additionally or alternatively, in some embodiments, step 502 is performed continuously by X-ray detector panel 120, such as when conserving power is not an issue for X-ray detector panel 120. For example, when X-ray detector panel 120 is connected to an external power source, step 502 can be performed continuously without draining a battery or other portable power supply included in X-ray detector panel 120.

In step 503, controller 210 controls or otherwise causes wireless module 230 to generate a first set of values for one or more wireless performance metrics for wireless module 230 and wireless module 240 to generate a second set of values for one or more wireless performance metrics for wireless module 240. In embodiments in which X-ray detector panel 120 includes additional wireless modules beside wireless modules 230 and 240, controller 210 causes each of the additional wireless modules to similarly generate respective sets of values for the wireless performance metrics. In some embodiments, controller 210 causes wireless module 230 to generate the first set of values for the wireless performance metrics and wireless module 240 to generate the second set of values for the wireless performance metrics simultaneously. That is, wireless module 230 generates at least a portion of the first set of values at the same time that wireless module 240 generates at least a portion of the second set of values.

The first set of values and the second set of values each include a value for each wireless performance metric employed in step 505, i.e., for determining wireless communication functions to be performed by wireless modules 230 and 240. In some embodiments, the first set and the second set each include a single value, and in other embodiments, the first set and the second set each include multiple values.

In some embodiments, the wireless performance metrics includes one or more metrics quantifying wireless performance of wireless module 230 and wireless module 240, including, without limitation, one or more of signal strength for a particular channel, data transfer rate for the particular channel, package retransmission rate for the particular channel (or package failure rate), latency associated with the particular channel, and the like. Any quantifiable measure may be included in the wireless performance metrics. It is noted that in embodiments in which multiple wireless interfaces (such as channels) are enabled by wireless module 230, in step 503, controller 210 controls wireless module 230 to generate a first set of values for the wireless performance metrics for each such interface.

In step 504, controller 210 receives the first set of values for the wireless performance metrics and the second set of values for the wireless performance metrics. Because the values included in the first set and second set are generally generated simultaneously, these values indicate the relative performance of each wireless interface for the current location of X-ray detector panel 120.

In step 505, controller 210 determines a first wireless communication function to be performed by wireless module 230 and a second wireless communication function to be performed by wireless module 240. In embodiments in which X-ray detector panel includes additional wireless modules, controller 210 also determines respective wireless communication functions for each of the additional wireless modules included in X-ray detector panel 120. Controller 210 bases the determination of step 505 on the first set of values for the wireless performance metrics and on the second set of values for the wireless performance metrics. In some embodiments, each set of values for the wireless performance metrics includes a single value, such as signal strength. In other embodiments each set of values for the wireless performance metrics includes multiple values. In such embodiments, the determination of step 505 may be based on a weighted combination of the multiple values. Thus, one value of the multiple values can be weighted more heavily than other values of the multiple values. For example, in one embodiment, signal strength has a weighting of 50%, data rate has a weighting of 30%, and packet failure rate has a weighting of 20%.

In step 505, the specific wireless communication function that is determined to be the first wireless communication function and the specific wireless communication function that is determined to be the second wireless communication function can vary depending on the configuration of X-ray detector panel 120 and on a current operating state of X-ray detector panel 120.

For example, in embodiments in which X-ray detector panel 120 is operating in an efficient power use state, the wireless module determined to have the weakest wireless performance may be powered off, and the wireless module determined to have the strongest wireless performance may be employed for both image data transfer and control signal transfer. For example, the wireless module determined to have the strongest wireless performance can transmit image data via a first channel and/or antenna with the strongest wireless performance, as determined in step 505, and transmit and receive control signals for X-ray detector panel 120 via a second channel and/or antenna with weaker wireless performance, as determined in step 505. Thus, in such an embodiment, the first wireless communication function includes performing both image data transfer and control signal transfer, while the second wireless communication function includes the appropriate wireless module powering off.

In embodiments in which X-ray detector panel 120 is operating in a fast image transfer state, the wireless module determined to have the weakest wireless performance may be employed to transmit and receive control signals for X-ray detector panel 120, and the wireless module determined to have the strongest wireless performance may be employed to upload image data from X-ray detector panel 120 to workstation 130 and/or to network 105. Thus, in such an embodiment, the first wireless communication function includes performing image data transfer, while the second wireless communication function includes performing control signal transfer.

In some embodiments, multiple wireless interfaces associated with a single wireless module can be employed to minimize or otherwise reduce transfer time of image data. In such embodiments, a wireless module of X-ray detector panel 120 transmits a first portion of image data acquired by X-ray detector panel 120 using a first channel and a second portion of image data acquired by X-ray detector panel 120 using a second channel. In some embodiments, the first portion of the image data is a first portion of a particular digital image or digital representation of an X-ray image and the second portion of the image data is a second portion of the particular digital image or digital representation of the X-ray image. In this way, image data associated with a single image acquired by X-ray detector panel 120 is partially uploaded via a first channel of a wireless module and partially via a second channel of the wireless module. In other embodiments, the image data acquired by X-ray detector panel 120 includes a digital video or other sequence of digital images. In such embodiments, the first portion of the image data is a first frame of the digital video or other sequence of digital images and the second portion of the image data is a second frame of the digital video or sequence of digital images. The first portion further includes a third frame or image, a fifth frame or image, and so on (e.g., every odd frame), while the second portion further includes a fourth frame or image, a sixth frame or image, and so on (e.g., every even frame). In this way, a sequence of digital video frames can be uploaded via two channels of a single wireless module of X-ray detector panel 120.

Alternatively or additionally, based on the wireless performance metrics received in step 504, controller 210 can determine additional wireless communication functions for one or more additional wireless interfaces. For example, in some embodiments, controller 210 selects one or more wireless interfaces associated with one or more other wireless modules to respectively transmit one or more additional portions of image data, thereby further increasing transfer rate of image data from X-ray detector panel 120. For example, when controller 210 determines in step 505 that one or more other wireless modules of X-ray detector panel 120 have a measured wireless performance that exceeds a minimum threshold value, controller 210 determines additional wireless communication functions for these one or more wireless modules of X-ray detector panel 120, such as transmitting the one or more additional portions of the image data.

In embodiments in which X-ray detector panel 120 is operating in a reliable image transfer state, the first wireless communication function includes performing a certain image data transfer, while the second wireless communication function includes performing the same image date transfer. Thus, in such embodiments, two wireless interfaces associated with X-ray detector panel 120 are employed in parallel to redundantly upload image date from X-ray detector panel 120. The two wireless interfaces may both be associated with a single wireless module, or one may associated with wireless module 230 and the other with wireless module 240.

In step 506, controller 210 causes the appropriate wireless modules of X-ray detector panel 120 to perform the wireless communication functions determined in step 505 and method 500 terminates.

A portable X-ray detector panel includes multiple wireless communication modules to enhance the wireless performance of the X-ray detector panel. Each wireless communication module is coupled to one or more respective antennas that are each disposed in a different portion or region of the X-ray detector panel. Consequently, each wireless communication module will have different reception/transmission capabilities. The X-ray detector panel dynamically allocates wireless interfaces associated with the multiple wireless communication modules to reduce power use, increase reliability of image transfer, and/or decrease transfer time if image data.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

I claim:

1. A X-ray imaging device, comprising:
   a first wireless communication module coupled to at least one antenna in a first set of antennas that is disposed within a first region of the device;
   a second wireless communication module coupled to at least one antenna in a second set of antennas that is disposed within a second region of the X-ray imaging device; and
   a controller that is coupled to the first wireless communication module and the second wireless communication module and is configured to:
      receive a first value for a wireless performance metric for the first wireless communication module while the X-ray imaging device is disposed in a current location;
      receive a second value for the wireless performance metric for the second wireless communication module while the X-ray imaging device is disposed in the current location;
      based on the first value and the second value, determine a first wireless communication function to be performed by the first wireless communication module; and
      cause the first wireless communication module to perform the first wireless communication function.

2. The X-ray imaging device of claim 1, wherein the controller is configured to:
   based on the first value and the second value, determine a second wireless communication function to be performed by the second wireless module; and
   cause the second wireless communication module to perform the second wireless communication function.

3. The X-ray imaging device of claim 1, wherein the first wireless communication module is configured with dual-band WiFi capability, and wherein the first wireless function comprises transmitting, using a first channel, image data associated with an image acquired by the X-ray imaging device and transmitting, using a second channel, the image data associated with the image.

4. The X-ray imaging device of claim 3, wherein the controller causes the first wireless communication module to perform the first wireless communication function and the second wireless communication module to perform the second wireless communication function simultaneously.

5. The X-ray imaging device of claim 1, wherein the first wireless communication module is configured with dual-band WiFi capability, and wherein the first wireless function comprises transmitting, using a first channel, a first portion of image data associated with an image acquired by the X-ray imaging device and transmitting, using a second channel, a second portion of the image data associated with the image.

6. The X-ray imaging device of claim 1, further comprising:
   a second antenna in the first set of antennas that is coupled to the first wireless communication module and is disposed within a third region of the X-ray imaging device; and
   a second antenna in the second set of antennas that is coupled to the second wireless communication module and is disposed within a fourth region of the X-ray imaging device.

7. The X-ray imaging device of claim 6, wherein the third region excludes the location of the second set of antennas and the fourth region excludes the location of the first set of antennas.

8. The X-ray imaging device of claim 6, wherein the first wireless function comprises transmitting, using the at least one antenna in a first set of antennas, a first portion of image data associated with an image acquired by the X-ray imaging device and transmitting, using the using the second antenna in the first set of antennas, a second portion of the image data associated with the image.

9. The X-ray imaging device of claim 8, wherein the second wireless function comprises receiving, using the at least one antenna in a second set of antennas, control signals for controlling the X-ray imaging device.

10. The X-ray imaging device of claim 1, wherein the first region includes a first surface of the device and the second region includes a second surface, and wherein the first surface is on an opposite side of the X-ray imaging device from the second surface.

11. The X-ray imaging device of claim 1, wherein the first region includes a first surface of the device and the second region includes a second surface, and wherein the first surface is adjacent to the second surface.

12. A method of allocating multiple wireless interfaces for a portable X-ray imaging device that includes a first wireless communication module and a second wireless communication module, the method comprising:
   receiving a first set of wireless performance metrics for the first wireless communication module while the X-ray imaging device is disposed in a current location;
   receiving a second set of wireless performance metrics for the second wireless communication module while the X-ray imaging device is disposed in the current location;
   based on the first set of wireless performance metrics and the second set of wireless performance metrics, determining a first wireless communication function to be performed by the first wireless communication module; and
   causing the first wireless communication module to perform the first wireless communication function.

13. The method of claim 12, further comprising:
   based on the first value and the second value, determining a second wireless communication function to be performed by the second wireless communication module; and
   causing the second wireless communication module to perform the second wireless communication function.

14. The method of claim 13, wherein the first wireless function comprises receiving control signals for controlling the X-ray imaging device and transmitting image data associated with an image acquired by the X-ray imaging device and the second wireless function comprises powering down the second wireless communication module.

15. The method of claim 14, wherein receiving the control signals comprises receiving the control signals using a first channel and transmitting the image data comprises transmitting the image data using a second channel.

16. The method of claim 13, wherein the first wireless function comprises receiving control signals for controlling the X-ray imaging device and the second wireless function comprises transmitting image data associated with an image acquired by the X-ray imaging device.

17. The method of claim 13, wherein the first wireless function comprises transmitting a first portion of image data acquired by the X-ray imaging device and the second wireless function comprises transmitting a second portion of the image data.

18. The method of claim 17, wherein the first portion of image data comprises data representing a first portion of an image acquired by the X-ray imaging device and the second portion of the image data comprises data representing a second portion of the image.

19. The method of claim 17, wherein the first portion of image data comprises data representing a first video frame acquired by the X-ray imaging device and the second portion of the image data comprises data representing a second video frame acquired by the X-ray imaging device.

20. The method of claim 13, wherein the controller causes the first wireless communication module to generate the first set of wireless performance metrics and the second wireless communication module to generate the second set of wireless performance metrics.

21. The method of claim 12, wherein the transmitting is performed in response to receipt of the control signals.

22. The method of claim 21, wherein the controller causes the first wireless communication module to generate the first set of wireless performance metrics and the second wireless communication module to generate the second set of wireless performance metrics simultaneously.

23. A non-transitory computer readable medium having instructions stored thereon adapted to perform the method of claim 12.

24. A portable system, comprising:
   a first wireless communication means;
   a second wireless communication means;
   means for receiving a first set of wireless performance metrics for the first wireless communication means;
   means for receiving a second set of wireless performance metrics for the second wireless communication means;
   based on the first set of wireless performance metrics and the second set of wireless performance metrics, means for determining a first wireless communication function to be performed by the first wireless communication means; and
   means for causing the first wireless communication means to perform the first wireless communication function.

* * * * *